(12) United States Patent
Santilli et al.

(10) Patent No.: US 9,480,480 B2
(45) Date of Patent: Nov. 1, 2016

(54) VASCULAR AND INTESTINAL OCCLUSION

(76) Inventors: Albert N. Santilli, Pepper Pike, OH (US); Robert Michler, Riverside, CT (US)

( * ) Notice: Subject to any disclaimer, the term of this patent is extended or adjusted under 35 U.S.C. 154(b) by 3000 days.

(21) Appl. No.: 11/610,836

(22) Filed: Dec. 14, 2006

(65) Prior Publication Data
US 2007/0149989 A1 Jun. 28, 2007

Related U.S. Application Data

(63) Continuation-in-part of application No. 11/315,799, filed on Dec. 22, 2005.

(51) Int. Cl.
*A61B 17/04* (2006.01)
*A61B 17/122* (2006.01)
*A61B 17/00* (2006.01)

(52) U.S. Cl.
CPC .. *A61B 17/1227* (2013.01); *A61B 2017/00243* (2013.01)

(58) Field of Classification Search
CPC .............. A61B 17/083; A61B 17/122; A61B 17/1227; A61B 17/0057; A61B 17/1285; A61B 17/10; A61B 17/128; A61B 2017/2837; A61B 17/0487; A61B 17/08; Y10S 227/902
USPC ................................................. 606/151–158
See application file for complete search history.

(56) References Cited

U.S. PATENT DOCUMENTS

| | | | |
|---|---|---|---|
| 3,746,002 A | 7/1973 | Haller | |
| 4,016,883 A | 4/1977 | Wright, Jr. | |
| 4,106,508 A | 8/1978 | Berlin | |
| 4,708,140 A | 11/1987 | Baron | |
| 4,988,355 A | 1/1991 | Leveen et al. | |
| 5,019,092 A | 5/1991 | Klintmalm | |
| 5,354,306 A * | 10/1994 | Garvey et al. | 606/157 |
| 5,447,515 A | 9/1995 | Robicsek | |
| 6,579,304 B1 | 6/2003 | Hart et al. | |
| 2005/0149068 A1 | 7/2005 | Williams et al. | |
| 2005/0149069 A1 | 7/2005 | Bertolero et al. | |
| 2005/0277959 A1* | 12/2005 | Cosgrove et al. | 606/151 |

* cited by examiner

*Primary Examiner* — Gregory Anderson
(74) *Attorney, Agent, or Firm* — Wayne D. Porter, Jr.

(57) ABSTRACT

A device for occluding a conduit includes first and second members, each with first and second ends. The second ends are connected by a hinge. The first ends interlock to close the device about the conduit. The members are shaped such that they can occlude the conduit without causing the development of damaged or necrotic tissue. If desired, a flexible cover can be provided and the first and second members can be disposed within the cover. If such a cover is used, it will contact the conduit in order to cushion the contact between the members and the conduit, minimize the tendency of the conduit to bleed, and increase traction relative to the conduit. The invention also includes methods for using the device to occlude a conduit.

14 Claims, 3 Drawing Sheets

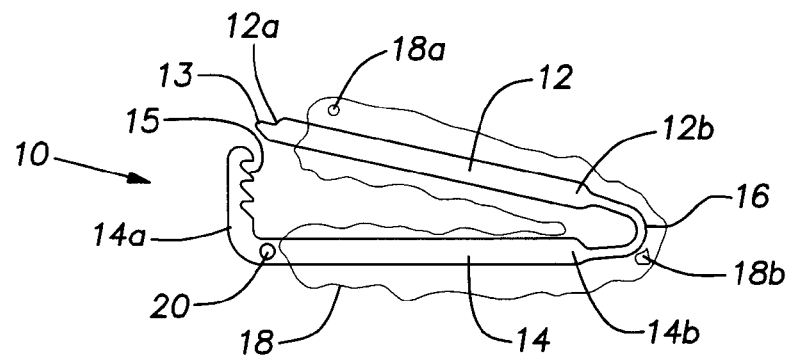
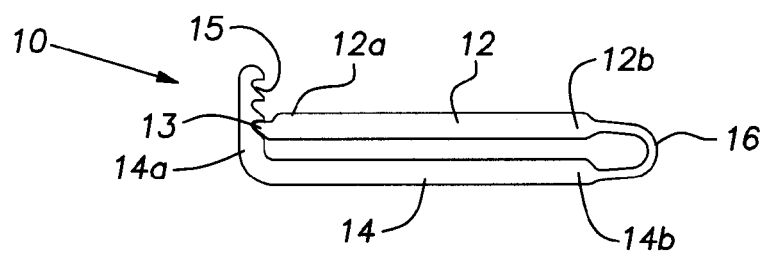
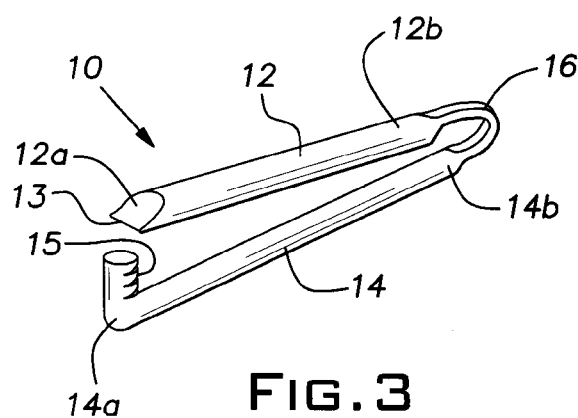
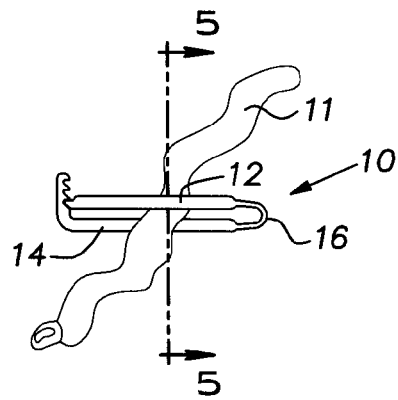
FIG. 1
FIG. 2
FIG. 3
FIG. 4

VASCULAR AND INTESTINAL OCCLUSION

REFERENCE TO RELATED APPLICATION

The present application is a continuation-in-part of application Ser. No. 11/315,799, filed Dec. 22, 2005 by Robert E. Michler and Albert N. Santilli, entitled Exclusion of the Left Atrial Appendage ("the LAA patent"), the disclosure of which is incorporated herein by reference.

BACKGROUND OF THE INVENTION

1. Field of the Invention

The invention relates to techniques for performing vascular and intestinal occlusion and, more particularly, to a clamp for such occlusion.

2. Description of the Prior Art

The body contains many conduits that accommodate a flow of fluids or semi-solids. Such conduits include the intestines and blood vessels, both veins and arteries. Many surgical procedures require that the flow in such conduits be reduced or halted ("occlusion") while surgical procedures such as anastomosis are performed. For convenience, any portion of the intestinal tract, any vascular member, or any other portion of the body that transports or convey fluids, semi-solids, or other material will be referred to herein as a "conduit" or "conduits."

Occlusion in conduits typically is accomplished by devices commonly referred to as clamps or clips. In general, these devices have opposing jaws that are adapted to extend over the conduit and to pinch the walls of the conduit against themselves in order to inhibit or stop flow through the conduit. The jaws commonly associated with clamps are relatively long and are operable by scissor-type handles which provide leverage for the jaws. Representative clamps of this type are shown in U.S. Pat. Nos. 5,019,092 and 5,447,515, the disclosures of which are incorporated herein by reference. Clamps commonly are used to occlude larger conduits such as the intestines. By comparison, the jaws of clips are relatively small and are biased by a spring commonly used to occlude smaller conduits such as blood vessels. As used herein, the term "clamp" will refer not only to clips and clamps, but also to other types of occlusion devices which have opposing jaws.

Conduits typically have a relatively smooth outer surface which often is wetted by body fluids such as blood. Attempts to occlude such conduits by pinching their walls must meet several objectives. The primary objective is to accomplish the occlusion, but of no less importance is a second objective, which is to maintain the clamp in place. Another objective is to occlude the conduit without causing tissue damage or necrosis, sometimes attributed to localized pressure or stress concentrations.

Traction is related to the resistance of the clamp to movement relative to the tissue. Theoretically, traction is equivalent to the product of the coefficient of friction, which is dependent upon the nature of the contacting surfaces, and the normal or clamping force. In the past, attempts have been made to increase this clamping force in order to increase the traction. Unfortunately, squeezing a conduit with a greater force tends to traumatize the tissue and in the case of blood vessels, destroy the intimal lining which cannot be regenerated. As a result, it is desirable to have only sufficient clamping force to achieve the first objective, that is, the occlusion of the conduit. Increasing the clamping force to achieve the second objective, that is, to increase traction, generally is not a suitable alternative.

Attempts have been made to increase the coefficient of friction in order to enhance the traction of the clamp relative to the conduit. This has been complicated by the wetness of the tissue surface of the conduit. U.S. Pat. No. 3,746,002 discloses an atraumatic surgical clamp having a plurality of pin members which extend though a resilient pad and which engage the tissue when the pad is compressed. Since the pins stick into the tissue, this produces a highly traumatic effect in most cases. Less aggressive attempts to increase the coefficient of friction have not always been sufficient to maintain the clamp in place, even after the conduit has been occluded.

Resilient pads, commonly referred to as inserts, have been provided for attachment to the inner surfaces of the opposing jaws. These inserts typically have a tissue-contacting surface which faces the opposing jaw, as well as a pair of side-surfaces which extend laterally of the insert. The inserts have been formed of resilient foam, in some cases with irregular surfaces. Other inserts have included fibers in the nature of toothbrush bristles to increase traction. Such inserts have experienced problems in either successfully occluding the conduit or in maintaining proper traction thereon. Examples of these various types of devices in question are shown in U.S. Pat. Nos. 4,106,508; 4,708,140; 4,98,355; and 6,579,304, the disclosures of which are incorporated herein by reference.

Unfortunately, although existing externally applied devices and techniques appear to offer a relatively simple and effective approach to the problem of occluding a conduit, a significant problem that remains is that of tissue damage, possibly even necrosis. If the compressive force that is applied to the conduit is too great, or if compression is localized in some areas and not others, the device either could cause undesired cell destruction or it could fail to perform its occlusion function properly.

Desirably, an externally applied exclusion device for a conduit would be available that would be easy to apply and remove. Any such device preferably would apply the proper amount of compressive force to occlude the conduit while avoiding any stress concentrations that would lead to undesired tissue damage or necrosis. Moreover, any such device hopefully would avoid punctures that would lead to difficult-to-control bleeding. Yet additionally, any such device would have adequate traction to maintain the device in its proper position on the conduit.

SUMMARY OF THE INVENTION

In response to the foregoing concerns, the present invention provides a new and improved technique for occluding conduits. The invention employs a device similar to that disclosed in the LAA patent and uses that device for occluding conduits. The device in question includes a first member having first and second ends adapted to extend from one side of a conduit to the other and to contact the conduit on a selected side thereof and a second member having first and second ends adapted to extend from one side of the conduit to the other and to contact the conduit on the other side thereof. The first and second members in use are disposed generally parallel with each other and are disposed sufficiently close to each other to compress the conduit between them without causing the development of necrotic tissue. Those portions of the first and second members that contact the conduit are configured to minimize stress concentrations in the conduit.

Preferably, those portions of the first and second members that come into contact with the conduit are rounded. It also is possible for the first and second members, in cross-section, to be rectangular with rounded ends, the longer dimension of the rectangle adapted to contact the conduit. The first and second members may be straight, or they can have a non-straight configuration such as arc-shaped when viewed from above. In the preferred embodiment, a hinge connects the second ends of the first and second members, the hinge comprising an integral extension of the second ends of the first and second members. The preferred embodiment also provides that the first ends of the first and second members interlock with each other to maintain the first and second members in a fixed position relative to each other.

It is possible to provide a flexible cover for the first and second members. The cover can be made of a number of materials that are biocompatible with the conduit and which provide suitable traction, but a flexible covering in the form of a mesh made of polyester fabric is preferred. Such a flexible cover will tend to cushion the contact between the conduit and the device and will assist in preventing undesired bleeding and movement of the device relative to the conduit.

The invention also includes a method for occluding a conduit comprising the step of providing a first, elongate member having first and second ends, the first member having a cross-section that will minimize stress concentrations in the conduit, the first member being long enough to extend from one side of the conduit to the other. The method also includes the step of providing a second, elongate member having first and second ends, the second member having a cross-section that will minimize stress concentrations in the conduit, the second member being long enough to extend from one side of the conduit to the other. The method provides for disposing the first and second members on either side of the conduit with the first and second members generally parallel with each other and for moving the first and second members sufficiently close to each other to compress the conduit between the first and second members without causing the development of necrotic tissue. The method also calls for maintaining the first and second members in a compressed position relative to the conduit.

Further embodiments of the method according to the invention include the step of providing a flexible container for the first and second members. The container is long enough to receive both the first and second members. The container is made of a material that is biocompatible with the conduit and that will increase the traction of the device on the conduit. The invention includes the step of placing the first and second members in the container prior to the step of disposing the first and second members on either side of the conduit with the longitudinal axes of the first and second members generally parallel with each other. If desired, and if the nature of the conduit permits, the method can include the step of suturing the flexible container to the conduit.

By using the present invention, a surgeon can quickly and easily occlude a conduit during the course of various surgical procedures such as anastomosis. The device according to the invention applies the proper amount of compressive force to occlude the conduit while avoiding stress concentrations that would lead to undesired tissue damage or necrosis. Moreover, the device will avoid punctures that would lead to difficult-to-control bleeding. The foregoing and other features and advantages of the invention will be apparent from a review of the following description of the invention, taken together with the attached drawings,

BRIEF DESCRIPTION OF THE DRAWINGS

FIG. 1 is a side elevation view of an occlusion device in accordance with one embodiment of the present invention, the embodiment shown being in an open position and having a flexible cover coupled thereto;

FIG. 2 is a view of the occlusion device of FIG. 1 with the cover removed and the device in a closed position;

FIG. 3 is a perspective view of the device of FIG. 1 with the cover removed and the device in an open position;

FIG. 4 illustrates the device of FIG. 1 as used on a conduit to occlude the conduit;

DESCRIPTION OF THE PREFERRED EMBODIMENT

Figure 5:
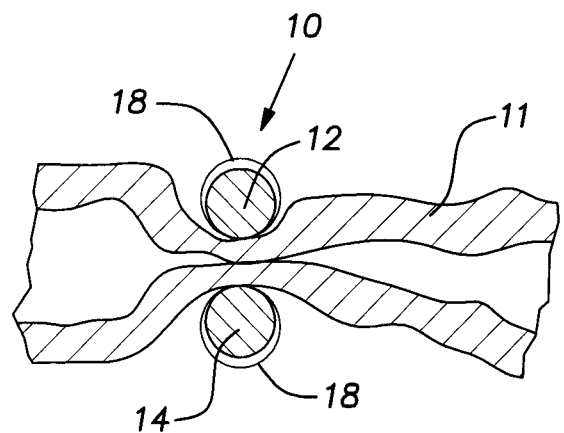
FIG. 5 is an enlarged sectional view taken along a plane indicated by line 5-5 in FIG. 4.

Referring to FIGS. 1-7, a device according to the invention is indicated generally by the reference numeral 10. The device 10 is intended to occlude a conduit 11. Such occlusion usually will occur on a temporary basis while a surgical procedure, such as anastomosis, is being performed on the conduit 11.

The device 10 includes a first member 12 and a second member 14. The first member 12 has a first end 12a and a second end 12b that lie in a first plane. The second member 14 also has a first end 14a and a second end 14b that lie in a first plane. The first member 12 and second member 14 are adapted to extend from one side of the conduit 11 to the other side and to contact, respectively, the conduit 11 on opposing sides thereof.

The occlusion device 10 preferably includes a hinge 16 that connects the second ends 12b, 14b. Preferably, the hinge 16 is generally U-shaped and constitutes an integral extension of the second ends 12b, 14b of the first and second members 12, 14. However, the hinge 16 may comprise any technique for connecting the first and second members 12, 14 at their ends 12b, 14b in such a manner that permits the first ends 12, 14a of the occlusion device 10 to be moved in the first plane between an open position (shown, for example, in FIGS. 1, 3, and 6) and a closed position (shown, for example, in FIGS. 2, 4, and 5). In the open position, the first ends 12a, 14a are spaced from each other (see FIGS. 2 and 4) such that the device 10 can be applied to the conduit 11 from the other side rather than the end. The hinge 16 preferably comprises a spring or is spring-tensioned so as to urge the first and second members 12, 14 away from each other.

Desirably, the first ends 12a, 14a of the first and second members 12, 14 interlock with each other to maintain the first and second members 12, 14 in the closed position—or, in other words, in a fixed position relative to each other. Preferably, the interlocking is accomplished by means of one or more teeth 15 located at end 14a, the teeth 15 interlocking with a blade 13 at end 12a. However, the occlusion device 10 may comprise any other suitable technique to maintain the occlusion device 10 in the closed position.

The device 10 may be made from any suitable biocompatible, sterilizable material such as stainless steel, tantalum, and, preferably, titanium, and alloys and combinations of any of the foregoing. Since the device 10 presumably will not be left in the body after the surgical procedure has been completed, the device 10 also can be made of other materials such as various plastics and the like.

Figure 6:
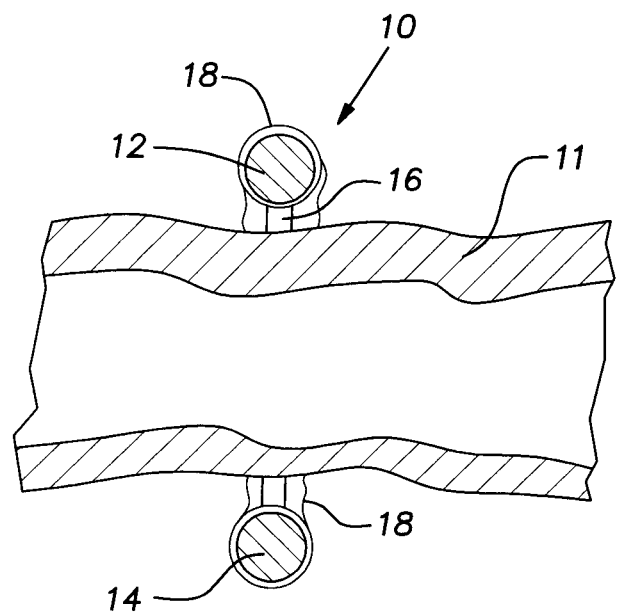
FIG. 6 shows the device of FIG. 5 in an open position.
Figure 7:
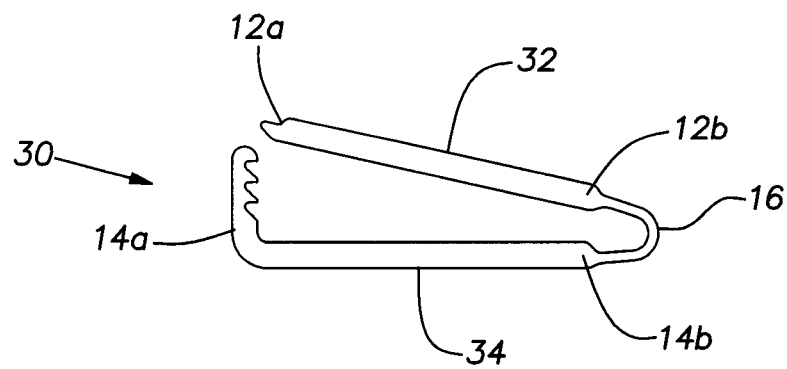
FIG. 7 is a side elevation view of an occlusion device in accordance with another embodiment of the present invention, the embodiment shown having arc-shaped first and second members.

In use, the first member 12 and second member 14 are placed in a closed position so as to dispose them generally parallel with each other and sufficiently close to each other to compress the conduit 11 between them and block the passage of fluids therethrough without causing the development of damaged or necrotic tissue (see FIGS. 4 and 5). The portions of the first member 12 and second member 14 that contact the conduit 11 are configured to minimize stress concentrations in the conduit 11. In preferred embodiments of the present invention, the portions of the first member 12 and second member 14 that contact the conduit 11 are rounded. In some embodiments, the first and second members 12, 14 are substantially round in cross-section, as illustrated in FIGS. 4, 6, and 7, for example. In other embodiments, the cross-section of the first and second members 12, 14 are each rectangular with rounded ends, the longer dimension of the rectangle adapted to contact the conduit 11. In embodiments wherein end 14a comprises multiple teeth, the occlusion device may have multiple closed positions so as to adapt to various thicknesses of the walls of the conduit 11. This latter feature may also help to minimize stress concentrations in the conduit 11. It is important to note that the portion of the occlusion device 10 that clamps against the tissue is smooth and has no teeth that press against and traumatize the tissue.

In some embodiments of the present invention, a flexible cover 18 is provided to cover the substantial length of the first and second members 12, 14. The cover 18 does not extend beyond the first ends 12a, 14a of the first and second members 12, 14 such that the device 10, when provided with the flexible cover 18, remains open at the first ends 12a, 14a of the first and second members 12, 14 when the first and second members 12, 14 are in the first, open position. Also, the interlock connection between the first ends 12a, 14a of the first and second members 12,14 is not covered. This permits the device 10 to be applied to the conduit 11 from the side rather than from the end. The cover 18 can be made of any material that is biocompatible with the conduit 11 and which increases the traction of the members 12, 14 on the conduit 11, but the preferred material is a polyester mesh. The cover 18, available preferably as variable density, tends to cushion the contact between the conduit 11 and the occlusion device 10 and assists in preventing undesired bleeding. An opening 20 in the occlusion device 10 may be provided for coupling the cover 18 to the occlusion device 10. For example, the cover 18 can be sewn to the occlusion device 10 via the opening 20. In appropriate circumstances, the cover 18 may also be further sewn to the conduit 11 or nearby portions of the patient's body at points 18a and 18b, for example.

Figure 8:
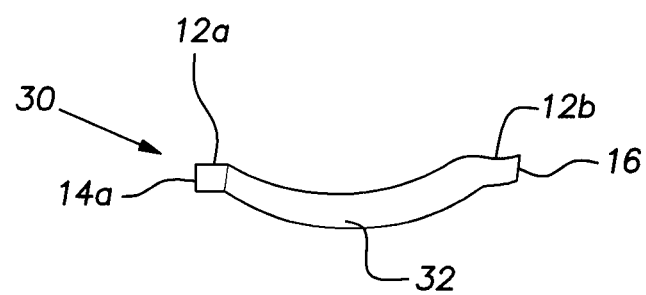
FIG. 8 is a top plan view of the device of FIG. 7 as used on a conduit to occlude the conduit.

Referring now to FIGS. 7 and 8, another embodiment of the present invention is indicated by the reference numeral 30. The embodiment 30 includes certain components identical or similar to those shown in the embodiment 10, and like reference numerals will be used where appropriate. In the embodiment 30, first and second members 32, 34 are comparable to first and second members 12, 14. However, the first member 32 and the second member 34 include central portions that are generally arc-shaped when viewed from above and lie in a second plane that is generally orthogonal to the first plane. First and second ends 12a, 12b are defined by straight segments that lie in the first plane and are disposed in a straight line relative to each other. The arc-shaped central portions lie out of the first plane. If desired, the cover 18 can be used with the embodiment 30.

As can be seen in FIG. 8, the shape of first and second members 32, 34 permits first and second members 32, 34 to be disposed toward or away from an operative site while in use. The arc-shaped feature of the members 32, 34 therefore permits clamping of the conduit 11 to occur closer to, or further away from, an operative site, while permitting hinging and locking to occur at a location somewhat away from the location where the conduit 11 is compressed.

According to one method of the present invention for occluding the conduit 11, a first member 12 is provided, the member 12 being elongate and having first and second ends 12a and 12b. The first member 12 has a cross-section that minimizes stress concentrations in the conduit 11, the first member 12 being long enough to extend from one side of the conduit 11 to the other. The method also includes the step of providing a second member 14, the member 14 being elongate and having first and second ends 14a and 14b. The second member 14 has a cross-section that minimizes stress concentrations in the conduit 11, the second member 14 being long enough to extend from one side of the conduit 11 to the other.

The method also provides for disposing the first and second members 12, 14 on either side of the conduit 11, the members 12, 14 being generally parallel with each other, and moving the first and second members 12, 14 sufficiently close to each other so as to compress the conduit 11 between the first and second members 12, 14 without causing the development of damaged or necrotic tissue. The method also includes maintaining the first and second members 12, 14 in a compressed position relative to the conduit 11.

The present invention also includes the step of providing a cover 18 as a flexible container for containing at least a portion of the first and second members 12, 14, the container being long enough to receive both the first and second members 12, 14 and being made of a material that is biocompatible with the conduit 11 and which increases traction relative to the conduit 11. The invention further includes the optional step of suturing the flexible container to the conduit 11. The invention also includes the optional step of providing the first and second members 12, 14 in an arc-shaped configuration so that clamping of the conduit can occur closer to, or further away from, an operative site.

As will be apparent from the foregoing description, the occlusion device 10 according to the invention is relatively easy to manufacture and simple to use. The occlusion device 10 provides a convenient way to temporarily occlude the flow of fluids or other material through a conduit while a surgical procedure such as anastomosis is being performed. All of this is accomplished in a manner that minimizes stress concentrations in the conduit 11 and the accompanying formation of damaged or necrotic tissue. The device 10 further avoids punctures that could lead to difficult-to-control bleeding.

Although the invention has been described in its preferred form with a certain degree of particularity, it will be understood that the present disclosure of the preferred embodiments has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A device for occluding a conduit, comprising:
   a first member having first and second ends adapted to extend from one side of the conduit to the other and to contact the conduit on a selected side thereof;

a second member having first and second ends adapted to extend from one side of the conduit to the other and to contact the conduit on the other side thereof;
the first and second ends of the first and second members lying in a first plane;
a hinge that connects the second ends of the first and second members, the hinge being generally U-shaped and constituting an integral extension of the second ends of the first and second members to establish a structure that is closed at the second ends of the first and second members and open at the first ends of the first and second members when the first and second members are in a first, open position;
the first and second members being generally arc-shaped when viewed from above and lying in a second plane that is generally orthogonal to the first plane;
the first ends of the first and second members being movable in the first plane from the first, open position in which the conduit can fit therebetween to a second, closed position in which the first and second members are disposed generally parallel with each other and being disposed sufficiently close to each other to compress the conduit between them without causing the development of damaged or necrotic tissue;
those portions of the first and second members that contact the conduit being configured to minimize stress concentrations in the conduit;
a flexible cover for the first and second members, the cover being biocompatible with the conduit and providing traction relative to the conduit; and
wherein the cover does not extend beyond the first ends of the first and second members such that the device, when provided with the flexible cover, remains open at the first ends of the first and second members when the first and second members are in the first, open position.

2. The device of claim 1, wherein those portions of the first and second members that come into contact with the conduit are rounded.

3. The device of claim 1, wherein the first and second members, in cross-section, are round.

4. The device of claim 1, wherein:
the first end of a selected one of the first or second members is defined by a protrusion disposed approximately at a right angle to the member from which it extends, the protrusion having a one tooth along its length; and
the first end of the other member is configured such that it can engage the tooth and thereby retain the first and second members in a fixed position relative to each other.

5. The device of claim 4, wherein the protrusion has a plurality of teeth along its length and the first end of the other member being configured such that it can engage a selected tooth.

6. The device of claim 1, wherein the flexible cover is a mesh made of polyester fabric.

7. The device of claim 1, wherein the material from which the first and second members is made is biocompatible with the conduit.

8. The device of claim 7, wherein the material from which the first and second members is made is selected from the group consisting of plastics materials and titanium, titanium alloys, stainless steel, tantalum, tantalum alloys, and mixtures thereof.

9. The device of claim 1, wherein the first and second ends of the first and second members have straight segments that lie in the first plane.

10. A device for occluding a conduit, comprising:
a first member having first and second ends adapted to extend from one side of the conduit to the other and to contact the conduit on a selected side thereof;
a second member having first and second ends adapted to extend from one side of the conduit to the other and to contact the conduit on the other side thereof;
the first and second ends of the first and second members lying in a first plane;
a hinge that connects the second ends of the first and second members, the hinge being generally U-shaped and constituting an integral extension of the second ends of the first and second members to establish a structure that is closed at the second ends of the first and second members and open at the first ends of the first and second members when the first and second members are in the first, open position;
the first and second members being generally arc-shaped when viewed from above and lying in a second plane that is generally orthogonal to the first plane;
the first end of a selected one of the first or second members being defined by a protrusion disposed approximately at a right angle to the member from which it extends, the protrusion having a one tooth along its length and the first end of the other member being configured such that it can engage the tooth and thereby retain the first and second members in a fixed position relative to each other the first ends of the first and second members being movable in the first plane from the first, open position in which the conduit can fit therebetween to a second, closed position in which the first and second members are disposed generally parallel with each other and being disposed sufficiently close to each other to compress the conduit between them without causing the development of damaged or necrotic tissue;
those portions of the first and second members that contact the conduit being rounded to minimize stress concentrations in the conduit;
a flexible cover for the first and second members, the cover being made of a material biocompatible with the conduit and which provides traction relative to the conduit; and
wherein the cover does not extend beyond the first ends of the first and second members such that the device, when provided with the flexible cover, remains open at the first ends of the first and second members when the first and second members are in the first, open position and the protrusion and the first end of the other member are exposed.

11. The device of claim 10, wherein the material from which the first and second members is made is selected from the group consisting of plastics materials and titanium, titanium alloys, stainless steel, tantalum, tantalum alloys, and mixtures thereof.

12. The device of claim 10, wherein the protrusion has a plurality of teeth along its length and the first end of the other member being configured such that it can engage a selected tooth.

13. The device of claim 10, wherein a selected one of the first and second members has an opening, and the cover is connected to the first and second members by being sewn to the opening.

14. The device of claim 10, wherein the first and second ends of the first and second members have straight segments that lie in the first plane.

* * * * *